United States Patent [19]

Melton

[11] Patent Number: 5,350,381

[45] Date of Patent: Sep. 27, 1994

[54] ORTHOPEDIC BROACH HANDLE APPARATUS

[75] Inventor: Mark Melton, Memphis, Tenn.

[73] Assignee: Smith & Nephew Richards Inc., Memphis, Tenn.

[21] Appl. No.: 29,770

[22] Filed: Mar. 11, 1993

[51] Int. Cl.⁵ .................... A61F 5/04; B23D 71/04
[52] U.S. Cl. .............................. 606/85; 29/80; 279/77; 409/287
[58] Field of Search ............... 29/80, 242; 279/77; 30/337, 339, 340; 409/287; 16/114 R; 606/79, 83, 84, 85

[56] References Cited

U.S. PATENT DOCUMENTS

| | | | |
|---|---|---|---|
| 20,010 | 4/1858 | Whittemore | 279/77 |
| 37,196 | 12/1862 | Kelly | 279/77 |
| 2,639,158 | 5/1953 | Procos | 279/77 |
| 3,243,213 | 3/1966 | Proctor | 287/119 |
| 4,011,657 | 3/1977 | Vance | 30/377 |
| 4,055,185 | 10/1977 | Waldron | 279/77 X |
| 4,218,940 | 8/1980 | Main | 81/63 |
| 4,306,550 | 12/1981 | Forte | 128/92 E |
| 4,583,270 | 4/1986 | Kenna | 29/80 |
| 4,587,964 | 5/1986 | Walker et al. | 128/92 |
| 4,601,289 | 7/1986 | Chiarizzio et al. | 128/305 |
| 4,614,457 | 9/1986 | Sammon | 403/322 |
| 4,739,750 | 4/1988 | Masse et al. | 128/92 VJ |
| 4,765,328 | 8/1988 | Keller et al. | 128/303 R |
| 4,990,149 | 2/1991 | Fallin | 606/85 |

Primary Examiner—Z. R. Bilinsky
Attorney, Agent, or Firm—Pravel, Hewitt, Kimball & Krieger

[57] ABSTRACT

A broach handle for use with an orthopedic broach includes an elongated handle having one end portion for making a connection with the broach and another end portion for gripping by the user and having an anvil that allows the handle to be hammered. A rotating locking member is carried in a slot at the distal end portion of the handle. The rotating locking member has inclined surfaces that allow the broach to separate from the handle when the inclined surface is positioned adjacent the broach. The rotating locking member also includes a thickened portion that forms a connection with the broach when positioned adjacent the broach.

9 Claims, 3 Drawing Sheets

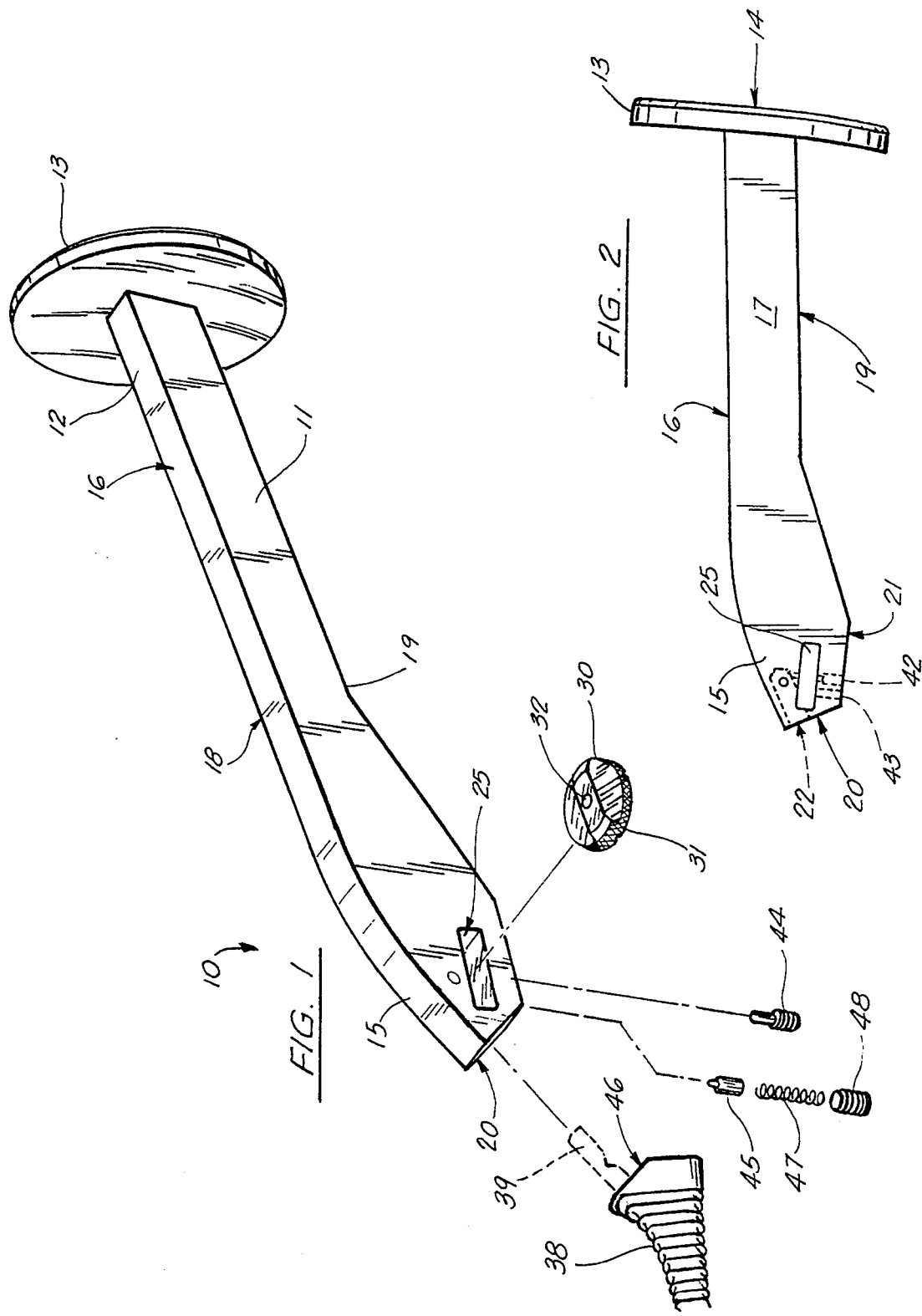

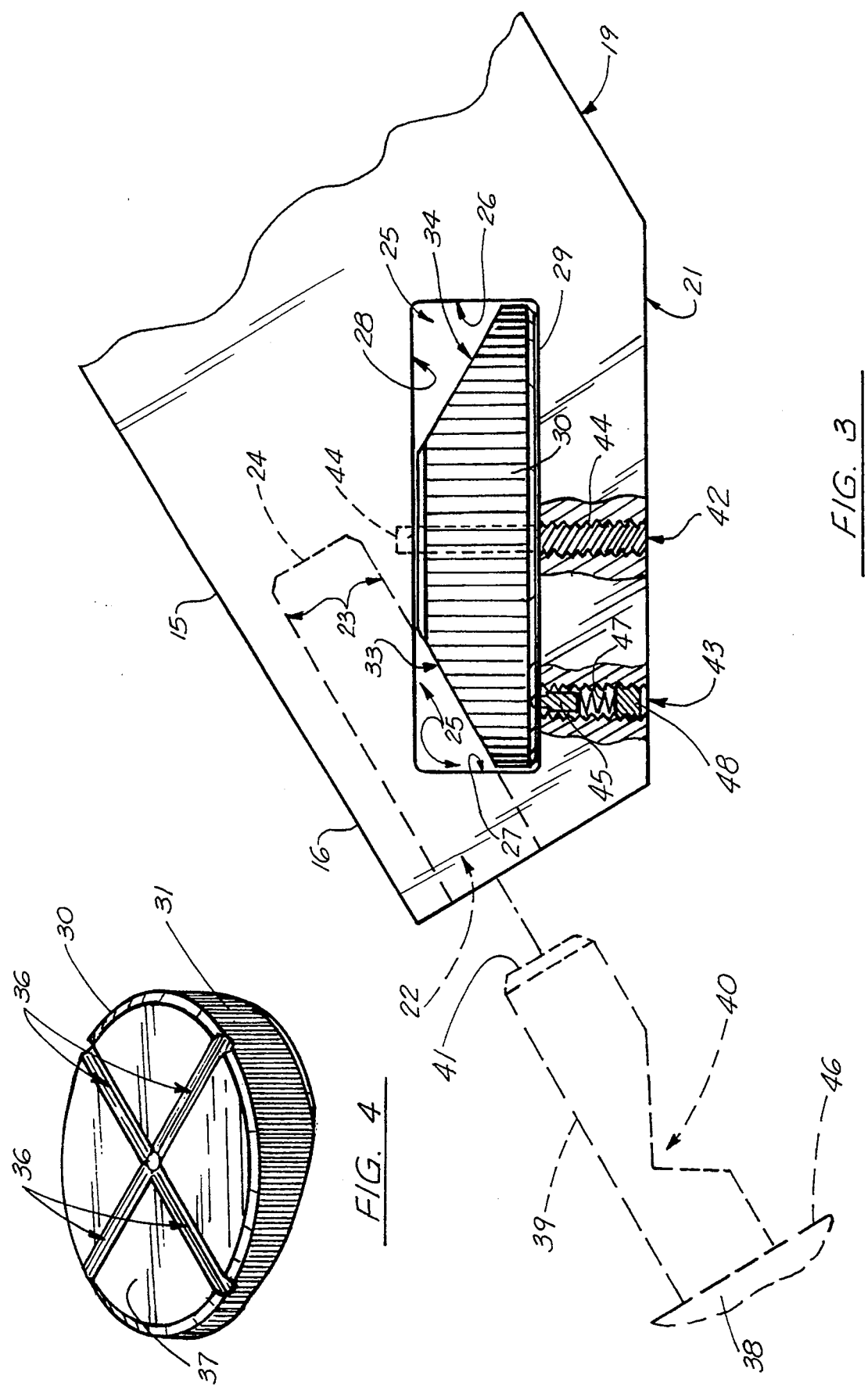

ORTHOPEDIC BROACH HANDLE APPARATUS

BACKGROUND OF THE INVENTION

1. Field of the Invention

The present invention relates to broach handles for use in orthopedic implant surgery. More particularly, the present invention relates to a broach handle apparatus having a rotary locking mechanism for locking the broach to the handle, and wherein the rotary locking member has radially spaced apart locking and release portions so that rotation of the locking member alternatively locks or releases the broach from the handle.

2. General Background

A broach is used during hip arthroplasty. The surgeon uses the broach to prepare the inner surfaces of the intramedullary canal of the patient to receive a femoral hip prosthesis. This preparation of the intramedullary canal by the surgeon is designed to insure a proper fit between the patient's femur and the prosthesis. Various types of broach handles have been patented. Examples are shown in U.S. Pat. No. 4,306,550 entitled "Combination Including Femoral Rasp and Calcar Facing Reamer" U.S. Pat. No. 4,583,270 entitled "Rasp Handle", U.S. Pat. No. 4,601,289 entitled "Femoral Trial Prosthesis/Rasp Assembly", and U.S. Pat. No. 4,990,149 entitled "Releasable Orthopedic Broach Handle Apparatus".

SUMMARY OF THE INVENTION

The present invention provides an improved broach handle apparatus for use with an orthopedic broach that is used to prepare a patient's femur to receive a hip implant. The handle is for use with a broach that has a tapered roughened end portion and an upper end having a connector that is adapted to engage the handle in a removable fashion.

The device provides a handle body having a first end portion with a connection end adapted for connecting to an upper end portion of the broach. A second portion is adapted to be gripped by the user.

A socket is disposed at the first end portion of the handle body for receiving a portion of the broach thereunto. A slot is positioned at the distal end portion of the handle body and in communication with the socket.

A rotary disk is disposed upon a spindle within the slot for forming a connection between the handle and the broach. The rotating disk provides an inclined surface portion that allows the broach to be separated from the handle when the inclined surface portion is positioned in communication with the socket, adjacent the broach.

The handle body has generally parallel planar sides and the slot is transversely positioned at the distal end portion of the handle body extending between the respective planar sides.

The upper surface of the disk is preferably inclined at two radial positions, spaced approximately one hundred and eighty degrees (180°) apart.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 1 is an exploded perspective view of the preferred embodiment of the apparatus of the present invention;

FIG. 2 is a side view of the preferred embodiment of the apparatus of the present invention;

FIG. 3 is a side fragmentary view of the preferred embodiment of the apparatus of the present invention;

FIG. 4 is a perspective view of the locking disk portion of the preferred embodiment of the apparatus of the present invention;

DETAILED DESCRIPTION OF THE PREFERRED EMBODIMENT

Figure 5:
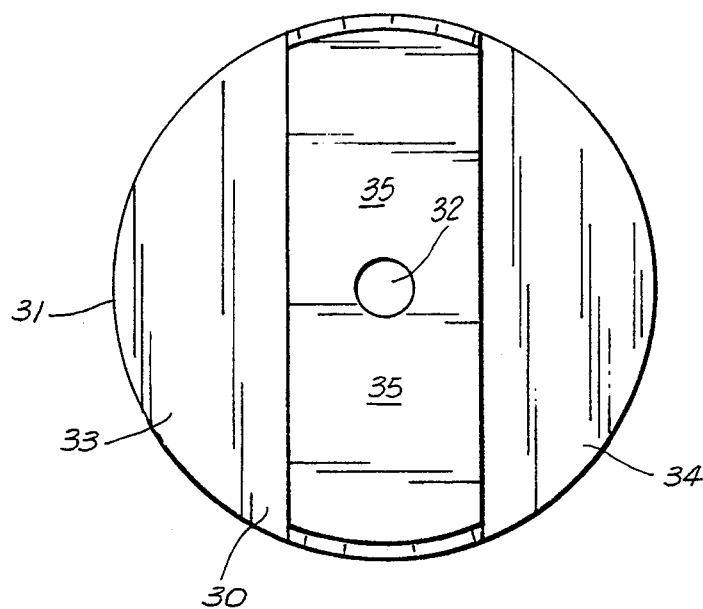
FIG. 5 is a top view of the locking disk portion of the preferred embodiment of the apparatus of the present invention.
Figure 6:
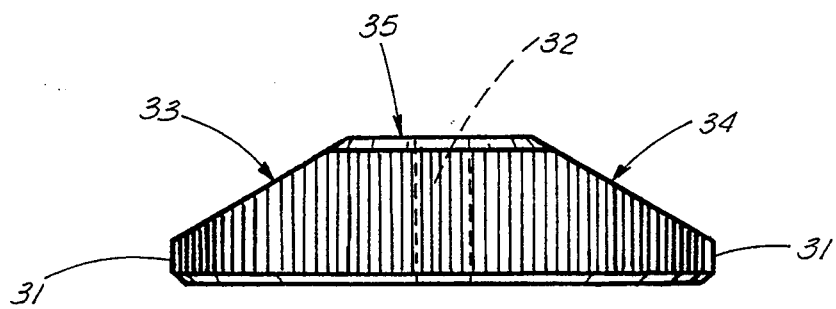
FIG. 6 is a side view of the locking disk portion of the preferred embodiment of the apparatus of the present invention.
Figure 7:
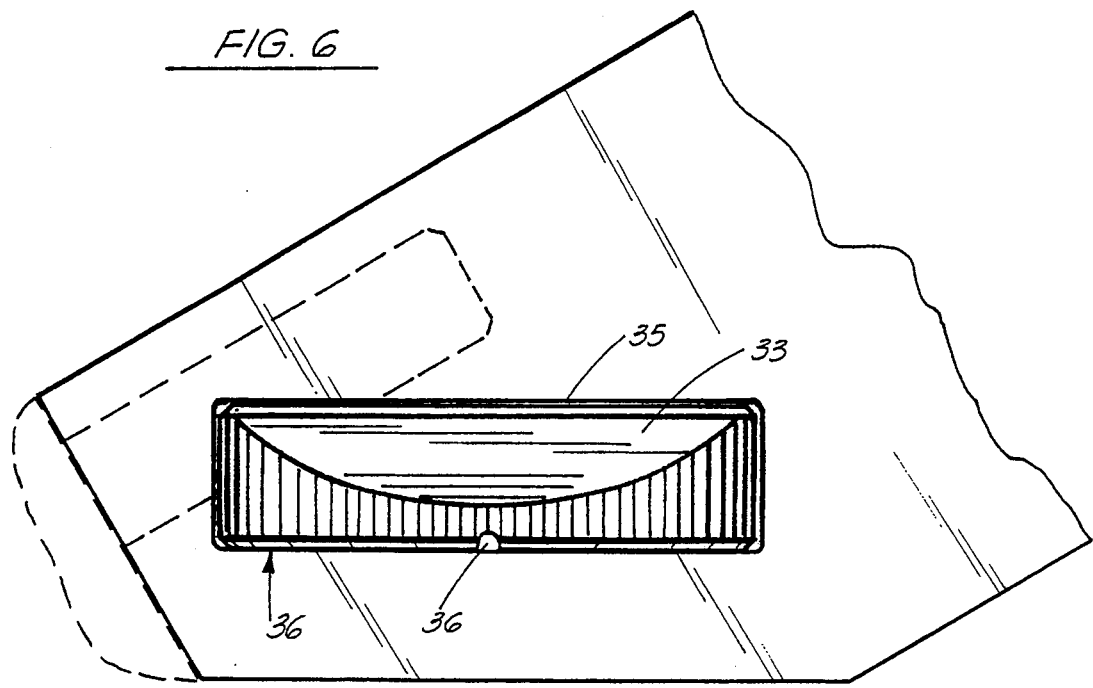
FIG. 7 is a fragmentary side view of the preferred embodiment of the apparatus of the present invention showing the rotary disk in locking position.

FIGS. 1–3 show generally the preferred embodiment of the apparatus of the present invention designated generally by the numeral 10. Broach handle 10 includes a handle body portion 11 having a proximal end 12 and a distal end 15. The proximal end 12 includes an anvil 13 in the form of a round disk. The anvil 13 has a flat surface 14 that can receive hammer blows for example during use of the broach handle apparatus 10 when the surgeon uses the handle 10 to support a broach 38 during broaching of the patient's proximal femur prior to placement of a hip prosthesis.

Handle 10 includes generally flat planar side portions 17, 18, a bottom surface 19 and an inclined end face 20. Surface 21 forms an angle with end face 20 as shown in FIG. 2.

A cylindrical socket 22 is receptive of attachment post 39 of broach 38. Socket 22 is generally cylindrically shaped as shown in FIG. 3 as defined by socket wall 23 and end wall 24 which is generally flat and circular. End 41 of post 39 registers with end wall 24 upon assembly of broach 38 and handle 10.

Transverse slot 25 communicates with socket 22 as shown in FIG. 3. Transverse slot 25 communicates with both sides 17, 18 of handle body 11.

Slot 25 is defined by four generally flat surfaces 26, 27, 28 and 29. A locking disk 30 is rotatably mounted within transverse slot 25. Locking disk 30 has an annular edge 31, a central opening 32 that is receptive of mounting pin 44. Pin 44 is mounted in opening 42. The upper surface of locking disk 30 includes a pair of radially spaced apart inclined surfaces 33, 34 and a radially extending flat surface 35 therebetween. The underside 37 of locking disk 30 is generally flat and circular, and provides a plurality of radial grooves 36. Each groove 36 functions as a "stop" position for dish 30, as spring loaded detent locking pin 45 registers into and grips each groove 36 as the disk 30 is rotated.

During use, broach 38 is affixed to broach handle body 11 by placing post 39 into cylindrical socket 22. Surface 20 mates with surface 46. In this fully engaged position, recess 40 of post 39 registers with transverse slot 25. A rotation of locking disk 30 places the disk 30 in either a locking or in a release position as selected by the user.

When one of the inclined surfaces 33, 34 aligns with post 39 and socket 22 as shown in FIG. 3, the inclined surface is spaced away from the socket wall 23 so that insertion and removal of the attachment post 39 is not hindered by the locking disk 30. A groove 36 aligns with pin 45 to fix the disk in this position.

Pin 45 occupies opening 43 and is spring loaded with coil spring 47. Plug 48 seals opening 43 behind spring 47. Plug 48 can be threadably engaged with similar threads in opening 43 adjacent surface 21. If the locking disk 30 is rotated ninety degrees (90°) from the position that is shown in FIG. 3, the flat surface 35 is aligned longitudinally with the body 11 so that the central axis of the surface 35 is generally parallel to the longitudinal axis of handle body 11. A groove 36 aligns with pin 45 to fix the disk in this position. The thickest portion of locking disk 30 now registers with both cylindrical socket 22 and recess 40. The maximum thickness of disk 30 is sized and shaped to completely register with recess 40 in the locked position so that removal of post 39 from socket 22 is prevented. The grooves 36 are v-shaped, and the top if pin 45 is rounded so that a user can overcome spring pressure to rotate the dish 30 from one position to another as selected.

The following table lists the part numbers and part descriptions as used herein and in the drawings attached hereto.

PARTS LIST

| Part Number | Description |
| --- | --- |
| 10 | broach handle |
| 11 | body |
| 12 | proximal end |
| 13 | anvil |
| 14 | flat surface |
| 15 | distal end |
| 16 | upper surface |
| 17 | side |
| 18 | side |
| 19 | bottom |
| 20 | end face |
| 21 | surface |
| 22 | cylindrical socket |
| 23 | socket wall |
| 24 | end wall |
| 25 | transverse slot |
| 26 | surface |
| 27 | surface |
| 28 | surface |
| 29 | surface |
| 30 | locking disk |
| 31 | annular edge |
| 32 | central opening |
| 33 | inclined surface |
| 34 | inclined surface |
| 35 | flat surface |
| 36 | radial groove |
| 37 | underside |
| 38 | broach |
| 39 | attachment post |
| 40 | recess |
| 41 | end of post |
| 42 | opening |
| 43 | opening |
| 44 | pin |
| 45 | detent locking pin |

PARTS LIST-continued

| Part Number | Description |
| --- | --- |
| 46 | surface |
| 47 | spring |
| 48 | plug |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A broach and handle apparatus; comprising:
    a) an orthopedic broach for preparation of the intramedullary canal of a bone to receive an implant, the broach including a tapered roughened portion and an upper end portion with a connector thereon,
    b) an elongated handle body portion having a first end portion with a connection end adapted for connecting to the upper end portion of the broach at the connector, and a second portion adapted to be gripped by a user;
    c) a socket disposed at the first end portion of the handle body for receiving the connector portion of the broach thereunto;
    d) a slot positioned at the distal end of the handle body and in communication with the socket;
    e) rotary means rotatably disposed within the slot about a rotational axis for forming a connection between the handle and the broach, the rotating member having a release surface portion that allows the broach to be separated from the handle when the release surface is positioned in the socket and adjacent the broach, wherein said release surface forms an acute angle with said rotational axis.

2. The broach handle apparatus of claim 1 wherein the handle body has generally parallel planar sides and the slot is transversely positioned at the distal end of the handle body extending to the respective planar sides.

3. The broach handle apparatus of claim 1 wherein the rotary means is an annular disk.

4. The broach handle apparatus of claim 3 wherein a portion of the disk has an inclined upper surface that forms an acute angle with the rotational axis.

5. The broach handle of claim 4 wherein the disk carries two inclined radially spaced apart surfaces.

6. The broach handle of claim 1 wherein the disk is circular and the center of the disk defines the rotational axis.

7. The broach handle of claim 1 further comprising locking means for affixing the position of the rotary means relative to the handle.

8. The broach handle of claim 1 wherein the rotary means comprises a rotating disk and an axle that supports the disk and the axle defines the rotational axis.

9. The broach handle apparatus of claim 1 wherein the release surface portion is an inclined surface.

* * * * *